United States Patent [19]

Modrovich

[11] 4,271,264
[45] Jun. 2, 1981

[54] STABILIZED LIQUID ENZYME AND COENZYME COMPOSITIONS

[76] Inventor: Ivan E. Modrovich, 1043 Mesa Dr., Camarillo, Calif. 93010

[21] Appl. No.: 862,106

[22] Filed: Dec. 19, 1977

Related U.S. Application Data

[63] Continuation-in-part of Ser. No. 722,565, Sep. 13, 1976, abandoned.

[51] Int. Cl.$^3$ .......................... C12Q 1/54; C12N 9/96
[52] U.S. Cl. ...................................... 435/14; 435/15; 435/26; 435/188; 435/190; 435/194
[58] Field of Search .............. 195/63, 68, 99, 103.5 R, 195/103.5 C; 435/4, 14, 17, 188, 15, 26, 190, 194

[56] References Cited

U.S. PATENT DOCUMENTS

| | | | |
|---|---|---|---|
| 3,539,450 | 11/1970 | Deutsch | 195/68 |
| 3,557,002 | 1/1971 | McCarty | 195/63 X |
| 3,627,688 | 12/1971 | McCarty et al. | 195/63 X |
| 3,721,607 | 3/1973 | Gruber et al. | 195/99 X |
| 3,761,420 | 9/1973 | Bogardus | 195/63 X |
| 3,764,478 | 10/1973 | Bergmeyer et al. | 195/99 |
| 3,776,900 | 12/1973 | Hammer | 195/63 X |
| 3,778,350 | 12/1973 | Bergmeyer et al. | 435/14 |

FOREIGN PATENT DOCUMENTS 2615958  11/1976  Fed. Rep. of Germany.

OTHER PUBLICATIONS

George et al., Stabilization of Lactate and Malate Dehydrogenase by Organic Solvents, Biochim. Biophys. Acta., vol. 191, 1969, (pp. 466-468).

*Primary Examiner*—David M. Naff
*Attorney, Agent, or Firm*—Romney, Schaap, Golant, Disner & Ashen

[57] ABSTRACT

Stabilized liquid enzyme and coenzyme compositions are prepared for use in biological diagnostic determination of glucose. In one embodiment a composition is prepared containing in admixture an aqueous vehicle, a nicotinamide-adenine dinucleotide coenzyme, a nucleotide, an enzyme including hexokinase and/or glucose-6-phosphate dehydrogenase and an organic solvent to stabilize the enzyme, coenzyme and nucleotide. The compositions have a pH of 6.0 to 8.5 and may contain a bacteriostat such as an azide compound. A preferred organic solvent is a polyol. In an alternative embodiment, a two reagent liquid enzyme and coenzyme composition is prepared wherein the enzyme is stabilized in one solution and the coenzyme and nucleotide stabilized in another solution, and the two solutions combined when used. In the enzyme-containing solution, an ammonia salt can be used as an alternative to the organic solvent to stabilize the enzyme. The compositions exhibit excellent shelf life and the container in which the compositions are stored can be repeatedly opened for use without any substantial degradation of the enzyme, coenzyme and nucleotide.

42 Claims, No Drawings

STABILIZED LIQUID ENZYME AND COENZYME COMPOSITIONS

RELATED APPLICATION

This application is a continuation-in-part of application Ser. No. 722,565 filed Sept. 13, 1976, now abandoned.

BACKGROUND OF THE INVENTION

I. Field of the Invention

This invention relates in general to certain new and useful improvements in biological determination reagent composition which permits the stabilization of enzymes and coenzymes in an aqueous media therein, and the method of stabilizing, and, more particularly, to such reagent composition and methods useful in determination of glucose in a biological fluid.

II. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years, and indications are that this trend wil continue. However, rigorous quality control measures are required to assure the accuracy and consistency of results. This requirement stems from the fact that the exact nature of enzymes, as well as the mechanisms of their action, remains unknown for the most part.

At present, the greatest limitation on the enzyme reagent manufacturer, by far, lies in the unstable characteristics of his products. Current methodologies require the use of numerous labile ingredients, and these ingredients are more likely to increase, rather than decrease, in number. Due to these severe restraints, rigorous quality control is required, and this quality control is, of course, costly. Moreover, if control in any step in the process is not maintained within high degree of control standards, the quality of the final product can be reduced materially.

The present commercial state of the art used for stabilizing the reactive ability of enzymes or coenzymes is by locking them into a solid matrix, either by freeze drying, dry blending such as used for tableting dried powders, primarily in the pharmaceutical diagnostic and related industries and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) lists the acceptable bottle-to-bottle variation of enzyme constituents at ±10% of the mean.

The present invention is uniquely designed so that the labile ingredients in a liquid enzyme solution are effectively "stabilized" by controlling the activity of the active sites of the enzyme and stabilizing a liquid coenzyme solution against reactivity. Both enzymes, coenzymes, including nucleotides, and substrates may be stabilized in the same solution, and in another embodiment enzymes may be stabilized in one solution and the coenzymes may be stabilized in another solution. This means of stabilization ensures long-term stability in a liquid media. Moreover, close tolerance control can be achieved in the manufacturing of a high quality product which eliminates the inconvenience of the rigid package size and the high cost of packaging and freeze drying and consequent reagent waste at the time of use.

OBJECTS OF THE INVENTION

It is, therefore, the primary object of the present invention to provide a liquid composition with coenzymes and/or enzymes which are packaged in a concentrated form and stabilized therein and diluted at time of use and which is stable after dilution for a significant length of time.

It is an additional object of the present invention to provide a stabilized composition of the type stated where the components may be packaged in a single container or where the enzymes can be separated from the coenzymes and packaged in two containers.

It is another object of the present invention to provide a composition of the type stated which has excellent shelf life and in which the container or containers may be repeatedly opened without substantial degradation of the labile components therein.

It is yet another object of the present invention to provide a labile coenzyme which may be stored in a liquid media, in the presence of another coenzyme and/or other labile enzymes, and all of which are stabilized against degradation.

It is a further object of the present invention to provide a labile enzyme and coenzyme composition of the type stated in an aqueous organic solvent media and where the stabilization of the enzyme and coenzyme does not affect the enzymatic reactivity after a substantial period of time.

It is also an object of the present invention to provide a method of stabilizing labile enzymes and/or coenzymes in a liquid media with relatively low-cost, commercially available stabilizing ingredients.

It is another salient object of the present invention to provide a method of stabilizing labile enzymes and/or coenzymes in the presence of other labile coenzymes or otherwise other labile coenzymes and which composition has a long shelf life.

It is yet a further object of the present invention to provide a method of stabilizing enzymes and/or coenzymes in the presence of a liquid media for a substantial period of time with a high degree of composition purity.

With the above and other objects in view, my invention resides in the novel compositions and the methods of making the same as hereinafter described in more detail.

SUMMARY OF THE INVENTION

Labile enzymes and coenzymes are treated according to the invention, resulting in long-term stability without affecting enzymatic or coenzymatic reactivity or phometric absorptivity. The invention provides reagents where quality control is assured throughout manufacturing, packaging, storage and use. The inconvenience of rigid package size is eliminated as is the high cost of packaging, freeze drying and reagent waste. Liquid enzyme and coenzyme systems provide application flexibility and separation of the ingredients is easily accomplished with negligible manufacturing cost providing the flexibility of triggering the desired reaction after all side reactions have been dissipated.

The stabilized enzymes and coenzymes of the invention have been assessed in studies which compared respective liquid enzyme and liquid coenzyme reagents with fresh reagents. The studies show a 1:1 correlation between aged liquid and fresh reagents with comparable sensitivity and precision. Providing enzyme, coenzyme and other labile ingredients in a stable liquid form enhances the colorimetric applicability of present day NAD/NADH coupled methodologies, as well as other methodologies, primarily because the separation of ingredients is easily accomplished. Stable liquid reagents are especially advantageous where NADH and other coenzyme consumption is the basis of measurement, and the color reagent must be separated from NADH and the reaction main. In the ultraviolet mode, the liquid system offers better reagent homogeneity and packaging, as well as flexibility in usage, in contrast to the freeze-dried or dry media preparation.

In diagnostic enzymology, the stabilization of enzyme, coenzyme and other labile biological reagents in a ready-to-use liquid media is a new and exciting approach to satisfy the needs of the clinical laboratory and the reliability demands of the regulatory authorities. The flexibility of liquid enzyme and coenzyme systems ensures their applicability to automated instrumentation, as well as their convenience in manual testings.

The liquid media which is designed to provide for stabilization of enzymes and coenzymes as hereinafter described is uniquely formulated so that one or more coenzymes may be stabilized in the media. Otherwise, one or more enzymes may be stabilized in the liquid media. Moreover, both coenzymes and enzymes may be stabilized in the same liquid media in a single container.

In Applicant's copending application Ser. No. 722,565, filed Sept. 13, 1976, certain specified liquid stabilized enzyme and coenzyme reagent compositions and the methods for producing the same were described. Certain of these components are effective in the biological determination of serum glucose. However, it has now been found that a highly effective reagent composition can be achieved by preparing the same in a concentrated state and which is thereafter diluted at the time of use. In this way, it is possible to dilute the composition and effectively make a determination even for a period of up to twenty-four hours, even after the serum glucose is added.

The prior art has known of compositions in which labile coenzymes, such as NADH for example, and labile enzymes, such as MDH or LDH, were stabilized in the presence of a relatively small concentration of a polyol. A polymer was also used in the stabilization process. Moreover, these compositions could also be used in the determination of glucose and biological constituents in other enzymes. However, these prior art compositions are not as effective as the compositions described herein.

The compounds ADP, ATP and AMP are chemically in the form of nucleotides. However, these compounds AMP, ADP, and ATP are often referred to herein as coenzymes or cofactors, even though they are classically nucleotides. Thus, the ADP, ATP and AMP will be referred to as coenzymes or cofactors herein to conform to standard nomenclature often used for these compounds and since they do in fact constitute an integral and important part of a coenzyme structure.

In accordance with the present invention, two composition forms are provided. The first of these composition forms resides in a composition which may be packaged in a single container. A second composition form is provided with the enzyme packaged in one container and stabilized therein in an aqueous media, and the coenzymes and other labile components packaged in another container and stabilized in an aqueous media in the other container.

In the case of the present invention, a gelatin polymer or other form of polymer is not required due to the fact that the polyol or other organic solvent is used in a much greater quantity.

In the single reagent composition form, a coenzyme, such as nicotinamide-adenine dinucleotide (NAD), is added to an aqueous vehicle along with another coenzyme which actually serves as a cofactor and sometimes as a substrate such as adenosin triphosphate (ATP). In addition, if desired, a magnesium enzyme activator, generally a magnesium salt, may be added, although the magnesium salt can be added at the time of use.

A buffering agent, such as tris (hydroxymethyl) aminomethane may also be added and the pH adjusted generally by means of a suitable acid, as for example, acidic acid. After the addition of the buffering agent, and perhaps the adjustment of the pH at that time, a suitable organic solvent, preferably a polyol such as glycerol, is added in an amount sufficient to stabilize the labile components. Thereafter, the labile coenzyme and the coenzyme in the form of a nucleotide are added and the pH may again be adjusted to the range of 6.0 to 8.5. After the pH has been stabilized within this range, the lyopholized enzymes may be added. In the case of determination of serum glucose, enzymes such as hexokinase (HK) and glucose-6-phosphate dehydrogenase (G-6-PDH) are added.

After all components have been added, the liquid stabilized solution is then dispensed into amber-glass or plastic bottles which are sealed in an air-tight container.

In another embodiment of the present invention in which the two container system is provided, the enzymes are stabilized in a single container in the presence of an excessive amount of the organic solvent and also in an aqueous media or in 1–4 molar aqueous ammonium sulfate or other salt solution. The coenzyme and the magnesium salt, if added at this time, the buffering agent are then stabilized in a separate aqueous media by glycerol, also in an excessive amount.

In either case, while the organic solvent may be present in an excessive amount, it only slightly inhibits enzymatic activity. However, since the serum glucose is being determined, and this is not an enzyme, the excessive amount of the organic solvent does not interfere with the determination. It is only important that the enzymes in solution do convert the reaction to the desired reaction products in a reasonable amount of time.

After the liquid stabilized enzyme solution and the coenzyme solution are prepared, they are then dispensed into individual amber-glass or plastic bottles and which are sealed in an air-tight condition. Moreover, these bottles are typically stored under refrigeration. The projected shelf life of the stabilized enzymes and coenzymes is up to two years at 2°–8° C. under these conditions without appreciable degradation.

It has been found in accordance with the present invention that the enzymes and coenzymes exhibit good solubility and stability in the aqueous miscible organic solvent. The envisioned chemical or physical reaction which provides for the stabilization of the enzymes and coenzymes is more fully described hereinafter.

These and other features and attendant advantages of the invention will become apparent as the invention becomes better understood by reference to the following general description and the following detailed description.

DETAILED DESCRIPTION

In the clinical diagnostic field, the commercial application of the present invention is represented by, but not limited to, the diagnostic reagents used to determine substrate concentration, as for example, glucose concentrations in biological fluids, and the like. Nevertheless, compositions prepared in accordance with the present invention can be used to determine and quantitate other biological constituents, as for example, the following constituents in biological fluids:

1. Glutamic-oxalacetic transaminase (SGOT)
2. Glutamic-pyruvic transaminse (SGPT)
3. Lactic dehydrogenase (LDH-P)
4. Lactic dehydrogenase (LDH-L)
5. Creatine Phosphokinase (CPK)
6. a-Hydroxybuteric dehydrogenase ($\alpha$-HBD)
7. Glucose (via Hexokinase-G-6-PDH)

These above identified reagents often react similarly, contain some common labile ingredients, and some of the chemical reactions involved are common. The following chemical reaction scheme is presented as a model to illustrate the general nature of the reactions involved:

REACTION SCHEME 1—GENERAL MODEL $$\text{SUBSTRATE(S)} \underset{pH}{\overset{\text{ENZYME}_1}{\rightleftarrows}} \text{PRODUCT(S)} \quad (1)$$

$$\text{PRODUCT/SUBSTRATE} + \text{NAD NADH}_2 \overset{\text{ENZYME}_2}{\rightleftarrows} \text{NADH}_2\text{-NAD} + \text{PRODUCT} \quad (2)$$

$$\text{NADH} + \text{CHROMOGEN} \overset{\text{CATALYST}}{\rightleftarrows} \text{CHROMOGEN} + \text{NAD} \quad (3)$$
$$\text{(oxidized)} \qquad\qquad\qquad \text{(reduced)}$$

All enzymatic reactions listed above, in accordance with this invention, will follow this general scheme, where reaction (2) is usually referred to as the coupling reaction, reactions (2) or (3) are the measuring reactions, and reaction (1) may be characterized as the primary reaction. It is understood, however, that not all three reactions are required for measurement; in fact, they may be limited to two, or one. In the case of the ultraviolet measurement of lactic dehydrogenase (LD) activity, for example, only reaction (2) is involved, as follows:

REACTION SCHEME 2—LDH $$\text{LACTATE} + \text{NAD} \overset{\text{LDH}}{\rightleftarrows} \text{NADH}_2 + \text{PYRUVATE}$$

REACTION SCHEME 3—GLUCOSE

The following reactions illustrate the determination of glucose by utilization of the coenzymes ATP and NAD.

$$\text{GLUCOSE} + \text{ATP} \underset{\text{MG}^{++}}{\overset{\text{HK}}{\rightleftarrows}} \text{G-6-P} + \text{ADP}$$

$$\text{G-6-P} + \text{NAD} \overset{\text{G-6-PDH}}{\rightleftarrows} \text{NADH} + \text{6-PHOSPHOGLUCONIC ACID}$$

$$\text{NADH} + \text{INT} \overset{\text{PMS}}{\rightleftarrows} \text{NAD} + \text{INT}$$
$$\quad\quad\quad\quad \text{(ox)} \qquad\qquad\qquad \text{(red)}$$

The enzyme which causes the primary reaction is hexokinase, and the enzyme which causes the coupling and measuring reaction is G-6-PDH. In the above reaction, the glucose is determined by measuring the NADH which is formed in the measuring reaction. In essence, the reaction is permitted to go to completion, and the amount of the coenzyme NADH formed is essentially measured.

Conversely, more than the three reactions listed may be involved, as in the case of creatine phosphokinase (CPK):

REACTION SCHEME 4—CPK $$\text{GP} + \text{ADP} \overset{\text{CK}}{\rightleftarrows} \text{ATP} + \text{CREATINE} \quad (1)$$

$$\text{ATP} + \text{GLUCOSE} \underset{\text{Mg}^{++}}{\overset{\text{HK}}{\rightleftarrows}} \text{GLUCOSE-6-PHOS.} + \text{ADP} \quad (2)$$

$$\text{GLUCOSE-6-PHOS.} + \text{NAD} \overset{\text{G-6-PDH}}{\rightleftarrows} \text{NADH}_2 + \text{GLUCONOLACTONE} \quad (3)$$

$$\text{NADH}_2 + \text{INT} \overset{\text{PMS}}{\rightleftarrows} \text{INT} + \text{NAD} \quad (4)$$
$$\quad\quad\quad\quad \text{(ox)} \qquad \text{(red)}$$

SYMBOLS

CP = Creatine phosphate
CPK = Creatine phosphokinase
ADP = Adenosine-5'-dishosphate
AM = Adenosine monophosphate
ATP = Adenosine triphosphate
HK = Hexokinase
NAD = Nicotinamide-adenine dinucleotide
NADP = Nicotinamide-adenine dinucleotide phosphate
$NADH_2$ = Nicotinamide-adenine dinucleotide, reduced
G-6-PDH = Glucose-6-phosphate dehydrogenase
G-6-P = Glucose-6-phosphate
INT = Tetrazolium salt
PMS = Phenazine methosulfate
SG = Serum glucose In this case, reactions (2) and (3) may be considered the coupling reactions, reactions (3) and (4) the measuring reactions, and reaction (1) the primary reaction.

Referring to REACTION SCHEME 1—GENERAL MODEL, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal physiological disorders.

Enzymes are large molecular weight, complex protein molecules, usually of unknown chemical structure. They are presently classified by their catalytic activity and extreme substrate specificity. Enzymes may be redefined as biological catalysts, capable of catalyzing a reaction of a single substrate, or a reaction of a similar group of substrates.

Coenzymes are lower molecular weight organic chemicals of well-defined structure, whose reactions or interactions are necessary for specific enzyme assay or reaction. They are catalyzed resulting in an irreversible change in the coenzyme's structure and/or atomic composition. Coenzymes are very useful in clinical assay procedure. Some have strong absorbance, their reactions are stiochiometric with the substrate and, therefore, the creation or disappearance of the absorbing form can be followed photometrically. Nicotinamide-adenine dinucleotide (NAD) and its reduced form ($NADH_2$) are used in many important clinical assays such as the S.G.O.T., S.G.P.T. and LDH assays previously described. NAD and $NADH_2$ have a molecular weight of about 700 and are complex organic molecules. $NADH_2$ absorbs strongly at 340 nm, whereas NAD does not absorb at this wavelength.

Substrates are organic chemicals of known structure, whose reactions or interactions are catalyzed by enzymes resulting in a change in the compound's structure, atomic composition, or stereochemical rotation. In general, substrates are prone to microbiological degradation as they serve as food for bacteria, fungi and other microorganisms. They are also subject to chemical hydrolysis in aqueous media but some of these compounds remain stable in aqueous media at or near neutral pH (i.e., pH range of 4–10). Typical substrates are glucose, lactate or lactic acid, gluconate and the like. By contrast, coenzymes in the form of nucleotides, such as ATP, ADP and AMP, are prone to hydrolysis.

In accordance with the present invention, the labile components are stabilized in an aqueous vehicle in a manner to be hereinafter described. Initially, the aqueous medium is maintained at a temperature within the range of about 15°–30° C. and, preferably, 20°–25° C. In some cases, it may be desirable to employ a metal, such as magnesium, which activates the enzyme(s) of a reaction when the stabilized composition is used. Magnesium, in the salt form of magnesium acetate is one of the preferred agents for this purpose. However, magnesium aspartate, magnesium acetate, magnesium fluoride, etc. may be used. This agent does not have to be incorporated in the stabilized compositions of the present invention and may be added at the time of use. This agent, which activates the coupling enzymes should be used in an amount of about 1 gram per liter to about 20 grams per liter and, preferably, about 4 grams per liter to about 10 grams per liter.

Thereafter, a buffering agent, such as a tris buffer, namely, tris(hydroxymethyl) aminomethane may be added. Typically, this buffering agent is added in an amount of about 2 grams per liter to about 100 grams per liter, and preferably from about 12 grams per liter to about 50 grams per liter, but at least sufficient to maintain the pH within a range of 6.0 to about 8.5. Other known buffering agents and other forms of buffering agents may also be employed in the process. In some cases, buffer salt of the type hereinafter described may be used. The buffer salt is added in an amount necessary to maintain the pH between 6.0 to 8.5. Generally, the buffer is a combination of 0.1–1% of an alkali metal hydroxide and 0.5 to 3% of an alkali metal acid carbonate or phosphate.

Other buffers which may be employed are certain azo compounds such as Imidazol, known as as glyoxalin ($C_3H_4N_2$), Pipes Buffer, i.e., Piperazine—$N,N^1$—bis (ethanesulfonic acid), Michaelis buffer, known also as the "Universal buffer" containing sodium acetate, diethyl barbituate, hydrochloric acid, and sodium chloride amino buffering agents, e.g., diethyl amine or triethylamine, etc. may be employed. Generally, any buffering agent which does not interfere with stabilization and enzymatic reactivity and maintain a pH in the range of 6.0 to 8.5 may be used.

Optionally, a bactericidal or fungicidal agent, preferably, an azide compound, such as sodium azide, may be added, typically, in amount of about 0.1% w/w. However, the amount of azide compound which is added can range from 0.01% to about 0.5%. In many cases, the azide salt or other bacteriostatic or fungacidal agent is not necessary and can be eliminated. Thus, the organic solvent in the aqueous media is generally sufficient to provide the required stabilization of the labile components. In some few cases, the azide salt must be eliminated inasmuch as it may have a tendency to interfere with stabilization, the reactions, or otherwise materially affect a substrate.

In addition to the foregoing, other bactericidal or other fungicidal agents which do not chemically react with a substrate or inhibit the enzymatic reaction may be employed. For example, some of these agents which may be used in addition to sodium azide are benzoic acid, phenol, thymol or pentachlorophenol.

After the addition of the metal, preferably a magnesium salt as indicated, and the bacteriostat or fungicidal agent, both of which may optionally be employed, it is then possible to add the desired coenzymes and nucleotides, and, in this case, the preferred coenzyme is NAD and the preferred nucleotide is ATP. The coenzyme NADP may be employed in place of the coenzyme NAD. As indicated above, the nucleotide ATP may actually function in the coupling reaction and, in this case, even constitutes a substrate.

The nucleotide ATP may be added in an amount of about 0.5 grams per liter to about 25 grams per liter and the amount is only limited by the solubility in the mixture inasmuch as the nucleotide ATP does not hinder the reaction. However, it should be understood that the nucleotide ATP could only be added up to its saturation point. In the preferred aspect of the invention, the nucleotide ATP is added in the amount of about 0.5 grams to about 12 grams. Thereafter, the NAD coenzyme or otherwise the NADP coenzyme, may be added and generally ranges from about 0.5 grams per liter to about 20 grams per liter, and preferably from about 2 grams to about 10 grams per liter.

As indicated previously, it is possible to form solutions of both stabilized enzymes and coenzymes. Thus, coenzyme and two or more enzymes may be stabilized in the same solution. For example, the nucleotide ATP may be stabilized in the manner as described herein. On the other hand, the NAD coenzyme may also be stabilized individually in the manner as described herein. Nevertheless, when stabilizing two or more coenzymes, the coenzymes may generally be added simultaneously or in any order.

NAD, while being unstable in water and in dry form when exposed to humid environments, is not nearly as unstable as its reduced form, $NADH_2$. Accordingly, the $NADH_2$ must be kept free of moisture, whereas the NAD may be packaged in a container with an aqueous solution, although stabilized in accordance with the present invention. Neither the exact mechanism, nor the end proucts, are of significance, except that the decomposed NAD can no longer effectively function as a coenzyme, nor does it possess the extinction coefficient at its characteristic wave length.

At this point in the process, and after all of the solid materials have been dissolved in the aqueous solution, the pH should again be adjusted to at least within the range of 6.5 to 8.0 or less, and preferably to about 7.5.

After adjustment of the pH, a suitable organic solvent, as for example glycerol, may be added. In this case, the glycerol or other solvent is added so that it constitutes from about 5% to about 60% v/v of the total composition and preferably from about 25% to about 50% v/v. Thus, in the overall range, glycerol or the other organic solvent may be added from about 100 milliliters to about 600 milliliters per liter of composition, and preferably from about 250 milliliters to about 500 milliliters based on an overall one liter composition.

The organic solvent should have the following characteristics:

1. pH range of 4 to 10;
2. Generally, liquid at room temperature;
3. Does not react with NAD or ATP and the like other than forming electrostatic (i.e., hydrogen) bonds;
4. Miscible with water;
5. Standard free energy of solvolysis is low (normal resonance is established).

The solvent must be miscible with water, liquid at room and refrigerator temperatures, and non-degradatively reactive with reactive sites of the enzymes and coenzymes other than formation of electrostatic bonds. Useful solvents are generally stable organic solvents such as ethers, ketones, sulfones, sulfoxides and alcohols such as methanol, ethanol, propanol, butanol, acetone, dioxane, DMSO, dimethylsulfone and THF. However, higher activity at lower solvent concentration for the treatment step is found for liquid polyol solvents. Liquid polyols containing from 2-4 hydroxyl groups and 2-10 carbon atoms are preferred, such as glycerol, ethylene glycol, propylene glycol or butane diol. Glycerol, propylene glycol, 1,2-propanediol, were found to possess all these qualities and are the solvents of choice.

When the selected organic solvent is a polyol, it is not necessary to use the azide compound, or, for that matter, other bacteriostatic agents, since the polyol effectively functions as a bacteriostatic agent. Nevertheless, while the selected solvent and the polymer provide the required stability in an aqueous solution, the azide compound is sometimes preferable, inasmuch as it appears to increase the coupling between the polymer and the enzymes and helps to prevent denaturation.

After the glycerol or other polyol is added, the pH of the solution thus formed is readjusted. Typically, the pH may be slightly basic and, therefore, a 1 normal HCl can be added in order to adjust the pH. In like manner, if the pH is slightly acidic, then a suitable base may be added to achieve a pH of 7.5.

One of the important aspects is that the coenzyme NAD is present in excessive amounts. As indicated, the determination of glucose is accomplished by measuring the NADH which is formed from the NAD. The NADH is unstable in an acidic environment and will degrade at a pH of 6 and, even more so, will degrade rapidly at a pH of 4. The pH of the solution is therefore maintained above a neutral pH of 7. While the NAD is actually more stable in the acid environment, it has been found in accordance with the present invention that it does not materially degrade in concentration specified in a slightly basic environment of a pH of 7.5. Nevertheless, the NAD is added in considerable excess so that there is always sufficient undegraded NAD present, even after several years in this liquid environment.

There is typically no maximum amount of coenzyme present, although the maximum amount will be limited by commercial practicalities. However, in all cases, the minimum and maximum amount of the coenzyme present will be pedicated on the requirements for stability and long shelf life in the stabilized liquid environment.

After the coenzymes and other components as specified above have been added to the liqid solution, the selected enzymes may be added. As with the case of the coenzymes, the enzymes may be added in any order. Again, one or more enzymes may be added to the solution. In the preferred aspect of the invention, and in accordance with the enzyme system identified above, the two enzymes are HK and G-6-PDH. The HK is also preferably added from about 100 IU per liter to about 30,000 IU per liter or more (pH of 7.6, 25° C). However, the preferred range is about 1000 to about 6000 IU of HK.

The G-6-PDH should, preferably, be formed from the L-mesenteroides bacteria if NAD coenzyme is used, or G-6-PDH from yeast if NADP is used, and should be concentrated in a range of about 100 IU per liter to about 30,000 IU per liter or above. In the preferred aspect of the invention, it is normally about 1,000–10,000 IU per liter of the G-6-PDH of this type which is used (pH of about 7.8 at 25° C.).

The enzymes should be present in an amount of at least 100 IU (International Units) per liter as indicated, although in most commercial reagents, the enzyme, as for example, the hexokinase, should be present at about a minimum of 1,000 IU per liter. In the normal commercial packages, the enzyme is present in about 1,000 to about 5,000 IU at a pH of 7.6 and a temperature of about 25° C. However, the maximum amount of the enzyme is unlimited, although normally, in almost all applications the amount of enzyme will not exceed 100,000 IU.

It is important in the process of the present invention that the enzymes are added after the final pH is adjusted. While the full mechanism for accomplishing the stabilization of the enzymes and coenzymes is not fully understood, it is believed that the selected solvent stabilizes the enzyme in the liquid media by protecting the functional group site, that is the part of the molecule where a substrate reaction may actually occur, or is otherwise catalyzed. Moreover, stabilization is believed to occur by protecting the enzymes and coenzymes from microbial contamination and chemical degradation such as hydrolysis. The coenzyme NAD differs from the coenzyme NADH in that the NAD will not appreciably dissolve in the selected solvent, such as propylene glycol. However, the NAD is more stable in water and the coenzyme does appear to be stabilized by the polyol. A pure polyol will denature the enzymes, but in the presence of an aqueous solution, such as a water-solvent mixture, the enzymes do not denature. Apparently, a polar group is required in the organic solvent to maintain the active sites of the enzymes in a stable condition. Obviously, some form of physical or chemical reaction occurs in the concentrated aqueous-organic solvent media, inasmuch as the enzymes and coenzymes retain catalytic activity and do not degrade enzymes and coenzymes retain catalytic activity and do not degrade in the specified concentrations.

It has been found that the above composition is quite effective and is stabilized for a relatively long period of time up to, for example, about two years under refrigeration conditions. In order to form a working solution, that is a solution used for determination of serum glucose for example, the stabilized liquid reagent composition is diluted with one part to about three parts of distilled water and mixed gently. After dilution, it has been found that the stabilization is reduced to about three to six months under refrigeration conditions. Moreover, it has been established that by virtue of the large amount of polyol or other organic solvent present the determination does not have to be made immediately and can be made within a period of up to 24 hours under normal room temperatures without any significant deterioration of the labile reaction product NADM, even after the serum glucose has been added, and the reaction proceeded to completion.

It has also been found in accordance with the present invention that it may be desirable to separate the stabilized enzymes from the stabilized coenzymes and other labile components. In this case, the various coenzymes as well as perhaps the magnesium salt or other metal salt and the possible bacteriostat or fungicidal agent may be stabilized in the manner as previously described.

In the two reagent compositions, the enzyme, as for example, G-6-PDH and HK are added to a container which has previously been provided with one of the organic solvents, as for example glycerol, and water in about a 50% mixture v/v. The amount of water in the mixture may range from about 30% to 70%, although it is desirable to have the organic solvent, and preferably the polyol, present in about the range of 45% to about 55% and, in a preferred aspect, 50% v/v.

Alternatively, in the two reagent composition form, the enzymes may be stabilized in a salt solution as opposed to the use of an organic solvent. Thus, the enzymes may be introduced in about a 1–4 molar ammonium sulfate salt solution or similar salt solution, although a 3 molar ammonium sulfate salt solution is preferred. The ammonium sulfate salt solution may range from about a 1.0 molar solution to about a 4.4 molar solution (saturated). In this respect, essentially any salt can be used to stabilize the enzyme for addition to the aqueous solution, as for example, many other ammonium salts, sodium chloride, and the like. The salt should be soluble in water at least at room temperature.

The second reagent is provided with the NAND or the NADP or even the NADH along with the ATP and the magnesium salt or other metallic salt. In addition, the second reagent may be provided with the bacteriostat or fungicidal agent, as may be desired. The metal or other magnesium salt, as for example, magnesium chloride, is present in an amount of about 0.25 grams per liter to about 5 grams per liter, and preferably from about 1 gram per liter to about 2.5 grams per liter. The buffering agent is added in an amount of about 3 grams per liter to about 25 grams per liter, and preferably from about 10 grams per liter to about 20 grams per liter, but at least sufficient to maintain the pH within the range of 6.0 to 8.5. The bactericidal or fungicidal agent, if used, is presently typically added in an amount of about 0.025% w/w, although the amount can range from about 0.0025% to about 1.25%.

The nucleotide ATP is added in the second reagent in an amount of about 0.125 grams per liter to about 6.2 grams per liter, and in the preferred aspect is added in an amount of about 1.5 grams to about 3 grams per liter. The other coenzymes such as the NAD or the NADP or otherwise the NAD coenzyme range from about 0.15 grams per liter to about 4 grams per liter, and preferably from about 1 gram per liter to about 3 grams per liter. The glycerol is also added to the second reagent composition in an amount of about 2.5% to about 20% v/v of the total composition, and preferably from about 6.25% to about 12.5% v/v, to reduce solution viscosity.

In order to form the working solution, that is the solution to enable determination of the serum glucose or other biological constituents, approximately 1 milliliter of the enzyme reagent is added to about 300 milliliters of the coenzyme reagent, and these two compositions are mixed gently. Prior to mixing of the two reagents forming part of the composition, the stability is up to two years under refrigeration conditions, and when mixed together the stability is reduced to about three to six months under refrigeration conditions.

One of the unique advantages of the compositions of the present invention is that the stabilized labile ingredients along with the enzmes are fully stabilized. Even moreso, the final reaction product NADH is stabilized after the serum glucose or other biological constituent is added. In the absence of the compositions of the present invention, photometric measurements must be made within thirty minutes, or otherwise the water would create instability of the NADH or the NADPH coenzymes produced.

When considering the reaction schemes set forth above for the analysis of serum glucose, it can be observed that the NADH or NADPH which is formed is measured photometrically and this is effectively a measure of the concentration of the serum glucose.

EXAMPLES

The invention is further illustrated by, but not limited to, the following examples:

EXAMPLE 1

Approximately 500 milliliters of water is maintaned at a temperature of about 20°–25° C. and thereafter 6.5 grams of a magnesum acetate salt, serving as an activator, is then added. Approximately 69 grams of a tris (hydroxymethyl) aminomethane is then added after which the solution is brought to a pH within the range of 6.5 to 8.0 by the addition of acidic acid.

Thereafter, 5–10 grams of ATP coenzyme and approximately 5–10 grams of the coenzyme is added to the solution.

Approximately 400 milliliters of glycerol is then added to the solution. Thereafter, additional acidic acid is added in order to maintain the pH within the range of 6.0 to 8.5.

After the pH has been stabilized, G-6-PDH enzyme is added in an amount sufficient to maintain 4–7000 IU per liter and the HK enzyme is also added in an amount to maintain 2–5000 IU per liter. Finally, water in an amount of approximately 100 milliliters is added in order to make a complete 1 liter solution of the composition.

After complete solution is attained, the solution is added to a plastic or glass container which is then closed. The containers are sealed and stored under refrigeration. It has been found that a stabilized composition in this manner provides storage stability of up to two years without significant degradation.

EXAMPLE 2

The sample produced in accordance with Example 1 is provided with about 0.1% w/w of sodium azide as a bacteriostat.

EXAMPLE 3

The sample of Example 1 is provided with the coenzyme NADP in place of the coenzyme NAD in substantially the same percentage and the same long shelf life is obtained without significant degradation.

EXAMPLE 4

The sample of Example 1 is provided with about 12.5 grams of ATP and 7.2 grams of NAD and the same long shelf life was obtained without significant degradation.

EXAMPLE 5

The sample of Example 1 is also reproduced except with 500 milliliters of glycerol with the addition of approximately 500 milliliters of water, and again the same long shelf life was obtained without significant degradation.

EXAMPLE 6

This example describes the two reagent compositions and the first reagent is made by taking approximately 300 milliliters of water which is maintained at a temperature of about 20°–25° C. Thereafter, 1.5 grams of a magnesium acetate salt, serving as an activator, is then added. Approximately 12 grams of a tris buffer is then added after the solution has been brought to a pH within the range of 6.5 to 8.0 by the addition of acidic acid.

Thereafter, approximately 2.5 grams of ATP coenzyme and approximately 2.5 grams of the NAD coenzyme are added to the solution.

Approximately 100 milliliters of glycerol is then added to the solution. Thereafter, additional acidic acid is added in order to maintain the pH within the range of 7.4 to 7.6. Finally, the reagent is then diluted wth water to obtain 1.0 liter of total solution and the pH is again adjusted.

In order to form the second reagent, 500 milliliters of water is maintained at a temperature of about 20°–25° C. and thereafter approximately 15 grams of a tris buffer is then added after the solution has been brought to a pH within the range of 6.5 to 8.0 by the addition of acidic acid.

Approximately 500 milliliters of glycerol is then added to the solution, with the addition of moe acidic acid in order to maintain the pH within the range of 6.0 to 8.5.

After the pH has been stabilized, G-6-PDH enzyme is added in an amount sufficient to maintain 20,000 I.U. per liter and the HK enzyme is also added in an amount to maintain 10,000 I.U. per liter.

After complete solution is attained, the two solutions are added to a plastic or glass container which is then closed. The containers are sealed and stored under refrigeration. It has been found that a stabilized composition in this manner provides storage stability of up to two years without significant degradation. Prior to use, 1 liter of the first reagent is combined with approximately 100 milliliters of the second reagent and the resulting solution is used for glucose determination.

EXAMPLE 7

The first reagent produced in accordance with Example 6 is provided with about 0.1% w/w of sodium azide as a bacteriostat.

EXAMPLE 8

The first reagent sample of Example 6 is provided with the coenzyme NADP in place of the coenzyme NAD in substantially the same percentage and the same long shelf life is obtained without significant degradation.

EXAMPLE 9

The sample of Example 6 is provided with about 12.5 grams of ATP and 7.2 grams of NAD and the same long shelf life was obtained without signficant degradation.

EXAMPLE 10

The sample composition of Example 6 was also reproduced except in the second reagent the enzymes were dissolved in 3 milliliters of water and 7 milliliters of 4.4 molar aqueous ammonium sulfate solution was added to complete 10 milliliters of total enzyme solution, and again, the same long shelf life was obtained without significant degradation. Again, the 10 milliliters second enzyme reagent was combined with 1.0 liter of the first (substrate) reagent prior to use. The combined reagent was found stable under refrigeration for 3–6 months.

It is to be realized that only preferred embodiments of the invention have been described and that numerous substitutions, modifications and alterations are permissible without departing from the spirit and scope of the invention as defined in the following claims.

Having thus described my invention, what I desire to claim and secure by letters patent is:

1. A stabilized liquid enzyme and coenzyme composition used in biological diagnostic determinations of glucose and which enzyme and coenzyme are normally unstable in an aqueous media, said composition comprising:

(a) at least 30% v/v of an aqueous vehicle, (b) at least a sufficient amount of nicotinamide-adenine dinucleotide coenzyme or a coenzyme having nicotinamide-adenine dinucleotide as a moiety thereof to perform a determination dissolved in said aqueous vehicle, (c) a nucleotide cooperating with the coenzyme or an enzyme in a determination reaction and which nucleotide has an adenosine moiety and a phosphate moiety, (d) at least 100 I.U. of at least one enzyme dissolved in said aqueous vehicle including at least hexokinase or glucose -6-phosphate dehydrogenase, and both said enzyme and coenzyme cooperating in a determination reaction such that glucose in a determination reaction can react with the nucleotide and ultimately permit generation of a further nicotinamide-adenine dinucleotide compound or a compound having nicotinamide-adenine dinucleotide as a moiety thereof which can be measured to enable a determination of glucose, (e) a non-reactive aqueous miscible polyol organic solvent dissolved in said aqueous vehicle and which is liquid at least at room temperature in said aqueous vehicle and present in an amount of about 5% to about 25% v/v based on the total composition, and which solvent is effective to stabilize the enzyme and the coenzyme and nucleotide in the presence of each other and in the presence of an aqueous vehicle, (f) and said composition having a pH from about 6.0 to about 8.5, such that the enzyme and coenzyme are stabilized.

2. The composition of claim 1 further characterized in that said composition comprises another enzyme selected from the class consisting of glucose-6-phosphate dehydrogenase, hexokinase, glutamate dehydrogenase, creatine phosphokinase, pyruvate kinase and alkaline phosphatase, and said coenzyme is selected from the class consisting of nicotinamide-adenine dinucleotide, nicotinamide-adenine dinucleotide phosphate; and nicotinamide-adenine dinucleotide reduced, and said nucleotide is selected from the class consisting of adenosine triphosphate, adenosine-5'-disphosphate and adenosine monophosphate.

3. The stabilized liquid composition of claim 1 further characterized in that said solvent has the following characteristics:

(a) pH of 10 to 4;
(b) liquid at room temperature;
(c) does not react with the coenzymes or enzymes other than forming electrostatic bonds;
(d) miscible with water;
(e) standard free energy of solvolysis is low.

4. The stabilized liquid composition of claim 1 further characterized in that said composition comprises hexokinase as a first labile enzyme and glucose-6-phosphate dehydrogenease as a second labile enzyme which is also stabilized by said solvent.

5. The stabilized liquid composition of claim 1 further characterized in that said composition comprises a bacteriostat which provides bacteriostatic action.

6. The stabilized liquid composition of claim 1 further characterized in that the bacteriostat is an azide compound.

7. The stabilized liquid composition of claim 1 further characterized in that said solvent has the following characteristics:

(a) pH of 4 to 10;
(b) Liquid at room temperature;
(c) Does not react with the coenzymes or enzymes other than forming electrostatic bonds;
(d) Miscible with water;
(e) Standard free energy of solvolysis is low.

8. The stabilized liquid composition of claim 1 further characterized in that said composition comprises the nucleotide adenosine-5'-triphosphate and a coenzyme selected from the class consisting of nicotinamide-adenine dinucleotide, nicotinamide-adenine dinucleotide, reduced, and nicotinamide-adenine dinucleotide phosphate and the composition comprises at least two enzymes including the enzyme hexokinase and the enzyme glucose-6-phosphate dehydrogenase.

9. The composition of claim 3 further characterized in that said nucleotide is present in an amount of about 0.5 to about 25 grams per liter and said coenzyme is present in an amount of about 0.5 to about 20 grams per liter, said enzymes are each added in an amount of about 1,000 to about 15,000 I.U. per liter of a final testing solution.

10. The composition of claim 3 further characterized in that said nucleotide is present in an amount of about 6 to about 12 grams per liter and said coenzyme is present in an amount of about 4 to about 10 grams per liter, said enzymes are each added in an amount of about 1,000 to about 15,000 I.U. per liter of solution.

11. The composition of claim 10 further characterized in that a buffering agent is present in an amount of about 0.01 to about 0.4 moles per liter, in a final testing solution.

12. A method of stabilizing a labile coenzyme and labile enzyme used in biological diagnostic determinations of glucose and which enzyme and coenzyme are normally unstable in aqueous media, said method comprising:

(a) mixing at least 30% v/v of water with an aqueous miscible non-reactive polyol organic solvent such that the solvent is present in an amount of about 5% to about 25% v/v based on the total composition to form an aqueous miscible organic solvent solution and which organic solvent is dissolved in the water and liquid at least at room temperature when so dissolved, (b) adding at least a sufficient amount per liter of a nicotinamide-adenosine dinucleotide coenzyme or a coenzyme having nicotinamide-adenine dinucleotide as a moiety thereof to said solution to perform a determination and which is dissolved in said solution and cooperates in a determination reaction, (c) adding a nucleotide cooperating with the coenzyme or an enzyme in a determination reaction and which nucleotide has an adenosine moiety and a phosphate moiety, (d) adjusting the pH to within the range of 6.0 to 8.5, such that the nucleotide and coenzyme are stabilized, (e) adding at least 1000 I.U. per liter of at least one labile enzyme including at least hexokinase or glucose-6-phosphate dehydrogenase to said solution, and which enzyme or enzymes is dissolved in said solution and cooperates in a determination reaction such that glucose in a determination reaction can react with the nucleotide and ultimately permit generation of a further nicotinamide-adenine dinucleotide compound or compound having nicotinamide-adenine dinucleotide as a moiety thereof which can be measured to enable a determination of glucose, and where said solvent is effective to stabilize the enzyme and the coenzyme and nucelotide in the presence of each other and in the presence of an aqueous vehicle, and, (f) sealing the composition.

13. The method of claim 12 further characterized in that said method comprises adding another enzyme selected from the class consisting of glucose-6-phosphate dehydrogenase, hexokinase, glutamate dehydrogenase, creatine phosphokinase, pyruvate kinase and alkaline phosphatase, and said coenzyme being selected from the class consisting of nicotinamide-adenine dinucleotide, nicotinamide-adenine dinucleotide phosphate, and nicotinamide-adenine dinucleotide, reduced, and said nucleotide is selected from the class consisting of adenosine triphosphate, adenosine-5'-diphosphate and adenosine monophosphte.

14. The method of claim 12 further characterized in that said method comprises adding a bacteriostatic agent to said composition.

15. The method of claim 14 further characterized in that said bacteriostatic agent is an azide compound.

16. The method of claim 12 further characterized in that said method also comprises hexokinase as a first enzyme, and said method comprises adding glucose-6-phosphate dehydrogenase as a second enzyme to said solution which is also stabilized therein, after adjustment of the pH.

17. The method of claim 13 further characterized in that said solvent has the following characteristics:
(a) pH between 4 to 10;
(b) Liquid at room temperature;
(c) Does not react with the enzymes or coenzymes other than forming electrostatic bonds;
(d) Miscible with water;
(e) Standard free energy of solvolysis is low.

18. The method of claim 17 further characterized in that the organic solvent contains 2-4 hydroxyl groups and 2-10 carbon atoms.

19. The method of making the stabilized liquid composition of claim 12 further characterized in that said composition comprises the nucleotide adenosine-5'-triphosphate and a coenzyme selected from the class consisting of nicotinamide-adenine dinucleotide, nicotinamide-adenine dinucleotide, reduced and nicotinamide-adenine dinucleotide phosphate, and the method comprises adding two enzymes including the enzyme hexokinase and the enzyme glucose-6-phosphate dehydrogenase.

20. The method of claim 13 further characterized in that said nucleotide is presented in an amount of about 0.5 to about 25 grams per liter and said coenzyme is present in an amount of about 0.5 to about 20 grams per liter, said first enzyme and a second enzyme are each added in an amount of about 1,000 to about 15,000 I.U. per liter of a final testing solution.

21. The method of claim 20 further characterized in that a buffering agent is added in an amount to contain 0.01-0.4 moles per liter of a final testing solution.

22. The method of claim 13 further characterized in that said nucleotide is present in an amount of about 6 to about 12 grams per liter and said coenzyme is present in an amount of about 6 to about 19 grams per liter, said first enzyme and a second enzyme are each added in an amount of about 1,000 to about 15,000 I.U. per liter of solution.

23. A two reagent liquid enzyme and coenzyme composition used in biological diagnostic determination of glucose and which enzymes and coenzymes are normally unstable in an aqueous media, said composition comprising:
(a) a first reagent comprised of:
(1) at least 30% v/v of a non-reactive aqueous vehicle;
(2) at least a sufficient amount of a nicotinamide-adenine dinucleotide coenzyme or a coenzyme having nicotinamide-adenine dinucleotide as a moiety thereof to perform a determination dissolved in said aqueous vehicle and cooperating in a determination reaction,
(3) a nucleotide cooperating with said coenzyme and an enzyme in a determination reaction, and which nucleotide has an adenosine moiety and a phosphate moiety,
(4) a non-reactive aqueous miscible polyol solvent present in an amount of about 2.5% to about 20% v/v dissolved in said aqueous vehicle and which is liquid at least at room temperature in said aqueous vehicle, and which solvent is effective in stabilizing the coenzyme and dinucleotide in the presence of an aqueous vehicle, and
(5) said first reagent having a pH of from about 6.0 to about 8.5, such that the coenzyme is stabilized,
(b) a second reagent comprised of:
(1) at least 30% v/v of a non-reactive aqueous vehicle,
(2) a stabilizer selected from the class consisting of
(i) an aqueous miscible polyol organic solvent dissolved in said aqueous vehicle and which is liquid at least at room temperature in said vehicle, said solvent being present in an amount of about 45% to about 55% v/v, and
(ii) about 1 to about 4.4 molar aqueous ammonia salt solution in said aqueous vehicle and which aqueous ammonia salt is soluble in water at least at room temperature,
(3) at least 100I.U. of at least one enzyme dissolved in said aqueous vehicle including at least hexokinase or glucose-6-phosphate dehydrogenase cooperating in a determination reaction and which is stabilized in the presence of said stabilizer and where the glucose in a determination reaction can react with the nucleotide and ultimately permit generation of a further nicotinamide-adenine dinucleotide compound or compound having nicotinamide-adenine dinucleotide as a moiety thereof which can be measured to enable a determination of glucose.

24. The stabilized liquid enzyme and coenzyme composition of claim 23 further characterized in that:
(a) said coenzyme is selected from the class consisting of nicotinamide-adenine dinucleotide, and nicotinamide-adenine dinucleotide phosphate,
(b) and said composition comprises another enzyme selected from the class consisting of glucose-6-phosphate dehydrogenase, hexokinase, glutamate dehydrogenase, creatine phosphokinase, pyruvate kinase and alkaline phosphatase,
(c) and said nucleotide is selected from the class consisting of adenosine triphosphate, adenosine-5'-diphosphate and adenosine monophosphate.

25. The stabilized liquid composition of claim 24 further characterized in that said first reagent comprises a bacteriostat which provides bacteriostatic action.

26. The stabilized liquid coenzyme composition of claim 24 further characterized in that said organic solvent has the following characteristics:
(a) pH between 4 to 10;
(b) Liquid at room temperature;
(c) Does not react with the coenzyme or enzymes other than forming electrostatic bonds;
(d) Miscible with water;
(e) Standard free energy of solvolysis is low.

27. The stabilized liquid composition of claim 23 further characterized in that said composition comprises the nucleotide adenosine-5'-phosphate and a coenzyme selected from the class consisting of nicotinamide-adenine dinucleotide, reduced and nicotinamide-adenine dinucleotide phosphate.

28. The composition of claim 24 further characterized in that said coenzyme is a first coenzyme which is present in an amount of about 0.5 to about 25 grams per liter, and said composition comprises a second coenzyme which is present in an amount of about 0.5 to about 20 grams per liter, said enzyme is a first enzyme, and said composition comprises a second enzyme, said first and second enzymes are each added in an amount of about 1,000 to about 15,000 I.U. per liter of a final testing solution.

29. The composition of claim 24 further characterized in that said coenzyme is a first coenzyme which is present in an amount of about 6 to about 12 grams per liter and said composition comprises a second coenzyme which is present in an amount of about 4 to about 10 grams per liter, said enzyme is a first enzyme and said composition comprises a second enzyme, said first and second enzymes are each added in an amount of about 1,000 to about 15,000 I.U. per liter of solution.

30. The composition of claim 29 in the form of a final testing solution formed by combining the first and second reagents and adding thereto a buffering agent to provide 0.01–0.4 moles per liter buffer in the final testing solution.

31. A method of stabilizing a labile enzyme and labile coenzyme in a two reagent composition used in biological diagnostic determination of glucose and which enzyme and coenzyme are normally unstable in an aqueous media, said method comprising:
(a) forming a first liquid stabilized reagent comprised of the steps of:
(1) dissolving a nicotinamide-adenine dinucleotide coenzyme or a coenzyme having nicotinamide-adenine dinucleotide as a moiety thereof in at least 30% v/v of an aqueous base and in an amount sufficient to perform a determination and which coenzyme cooperates in a determination reaction,
(2) adding a nucleotide cooperating with the coenzyme or an enzyme in a determination reaction and which nucleotide has an adenosine moiety and a phosphate moiety,
(3) dissolving in said coenzyme containing aqueous base about 2.5% to about 20% v/v of a non-reactive aqueous miscible polyol organic solvent to provide a stabilized composition and which solvent is liquid at least at room temperature in said aqueous base,
(4) adding a buffering agent to maintain the reagent pH to about 6.0 to about 8.5, and
(5) sealing the composition in a first container, (b) forming a second liquid stabilized reagent comprising the steps of:
(1) mixing at least 30% v/v of water with a stabilizer selected from the class consisting of:
(i) about 45% to about 55% v/v of an aqueous miscible polyol organic solvent to form a solution thereof and which organic solvent is dissolved in the water and liquid at least at room temperature in the water, and
(ii) about 1 to about 4.4 molar aqueous ammonia salt solution and which ammonia salt is soluble in water at least room temperature,
(2) dissolving at least 100 I.U. per liter of at least one enzyme including at least hexokinase or glucose -6-phosphate dehydrogenase in said solution to form the composition, and which enzyme cooperates in a determination reaction, such that glucose in a determination reaction can react with the nucleotide and ultimately permit generation of a further nicotinamide-adenosine dinucleotide compound or a compound having a nicotinamide-adenoisine dinucleotide moiety which can be measured to enable a determination of glucose, and
(3) sealing the composition in a second container.

32. The method of claim 31 further characterized in that:
(a) said coenzyme is selected from the class consisting of a nicotinamide-adenine dinucleotide, and nicotinamide-adenine dinucleotide phosphate,
(b) said second reagent comprises another enzyme selected from the class consisting of glucose-6-phosphate dehydrogenase, hexokinase, glutamate dehydrogenase, creatine phosphokinase, pyruvate kinase and alkaline phosphatase, and
(c) said nucleotide is selected from the class consisting of adenosine triphosphate, adenosine-5'-diphosphate and adenosine monophosphate.

33. The method of claim 30 further characterized in that said method comprises adding a bacteriostatic agent to said first reagent.

34. The method of claim 32 further characterized in that said organic solvent has the following characterstics:
(a) pH between 4 to 10;
(b) liquid at room temperature;
(c) does not react with enzymes and coenzymes other than forming electrostatic bonds;
(d) miscible with water,;
(e) standard free energy of solvolysis is low.;

35. The method of claim 32 further characterized in that the polyol contains from 2–10 carbon atoms and 2–4 hydroxyl groups.

36. A stabilized liquid enzyme and coenzyme composition used in biological diagnostic determinations of glucose and which enzyme and coenzyme are normally unstable in an aqueous media, said composition comprising:
(a) at least 30% v/v of an aqueous vehicle,
(b) at least a sufficient amount of a coenzyme to perform a determination dissolved in said aqueous vehicle, said coenzyme being selected from the class consisting of nicotinamide-adenine dinucleotide, nicotinamide-adenine dinucleotide phosphate, and dinucleotide, reduced,
(c) a nucleotide cooperating with the coenzyme or an enzyme in a determination reaction, said nucleotide being selected from the class consisting of adenosine triphosphate, adenosine-5'-diphosphate and adenosine monophosphate, (d) at least 100 I.U. of at least one enzyme dissolved in said aqueous vehicle including at least hexokinase or glucose-6-phosphate dehydrogenase, and both said enzyme and coenzyme cooperating in a determination reaction, such that glucose in a determination reaction can react with the nucleotide and ultimately permit generation of a further nicotinamide-adenine dinucleotide compound or a compound having nicotinamide-adenine dinucleotide as a moiety thereof which can be measured to enable a determination of glucose, (e) a non-reactive aqueous miscible polyol organic solvent containing from 2-4 hydroxyl groups and 2-10 carbon atoms dissolved in said aqueous vehicle and which is liquid at least at room temperature in the aquoeus vehicle and present in an amount of about 5% to about 25% v/v based on the total composition, and which polyol is effective in stabilizing the enzyme and the coenzyme and nucleotide in the presence of each other and in the presence of an aqueous vehicle, (f) and said composition having pH of from about 6.0 to about 8.5, such that the enzyme and coenzyme and nucleotide are stabilized.

37. The composition of claim 36 further characterized in that said composition comprises another enzyme selected from the class consisting of glucose-6-phosphate dehydrogenase, hexokinase, glutamate dehydrogenase, creatine phosphokinase, pyruvate kinase and alkaline phosphatase.

38. The stabilized liquid composition of claim 37 further characterized in that said composition comprises a first labile coenzyme and a second labile coenzyme.

39. The stabilized liquid composition of claim 36 further characterized in that said composition comprises a first labile enzyme which is hexokinase and at least one second labile enzyme which is glucose-6-phosphate dehydrogenase and which is also stabilized by said solvent.

40. The stabilized liquid composition of claim 36 further characterized in that said composition comprises a bacteriostat which provides bacteriostatic action.

41. The stabilized liquid composition of claim 40 further characterized in that the bacteriostat is an azide compound.

42. The composition of claim 37 further characterized in that said nucleotide is present in an amount of about 0.5 to about 25 grams per liter and said coenzyme is present in an amount of about 0.5 to about 20 grams per liter, said enzymes are each added in an amount of about 1,000 to about 15,000 I.U. per liter of a final testing solution.

* * * * *